(12) United States Patent
Ganesan

(10) Patent No.: US 10,799,171 B2
(45) Date of Patent: Oct. 13, 2020

(54) DETECTING ALLERGIC REACTION AND ALERTING A GUARDIAN DEVICE

(71) Applicant: Aetna Inc., Hartford, CT (US)

(72) Inventor: Sriram Ganesan, North Wales, PA (US)

(73) Assignee: Aetna Inc., Hartford, CT (US)

( * ) Notice: Subject to any disclaimer, the term of this patent is extended or adjusted under 35 U.S.C. 154(b) by 0 days.

(21) Appl. No.: 16/775,902

(22) Filed: Jan. 29, 2020

(65) Prior Publication Data

US 2020/0163611 A1 May 28, 2020

Related U.S. Application Data

(63) Continuation of application No. 16/022,025, filed on Jun. 28, 2018, now Pat. No. 10,588,562.

(51) Int. Cl.
| | |
|---|---|
| *A61B 5/00* | (2006.01) |
| *G08B 21/02* | (2006.01) |
| *A61B 5/0205* | (2006.01) |
| *A61B 5/1455* | (2006.01) |
| *A61B 5/08* | (2006.01) |
| *A61B 5/021* | (2006.01) |
| *A61B 5/024* | (2006.01) |

(52) U.S. Cl.
CPC ............ *A61B 5/411* (2013.01); *A61B 5/0022* (2013.01); *A61B 5/02055* (2013.01); *A61B 5/14552* (2013.01); *A61B 5/746* (2013.01); *G08B 21/0211* (2013.01); *G08B 21/0236* (2013.01); *G08B 21/0269* (2013.01); *A61B 5/021* (2013.01); *A61B 5/024* (2013.01); *A61B 5/0816* (2013.01)

(58) Field of Classification Search
CPC ... A61B 5/411; A61B 5/0022; A61B 5/02055; A61B 5/14552; A61B 5/746; G08B 21/0211; G08B 21/0236; G08B 21/0269
USPC ...................................................... 340/573.1
See application file for complete search history.

(56) References Cited

U.S. PATENT DOCUMENTS

| | | | | |
|---|---|---|---|---|
| 10,588,562 | B2 * | 3/2020 | Ganesan | A61B 5/0022 |
| 2011/0148626 | A1 * | 6/2011 | Acevedo | G01S 5/0027 |
| | | | | 340/539.13 |
| 2012/0245464 | A1 * | 9/2012 | Tran | A61B 5/0024 |
| | | | | 600/437 |
| 2018/0028106 | A1 * | 2/2018 | Leschinsky | A61B 5/4839 |
| 2018/0206722 | A1 * | 7/2018 | Gamez | A61B 5/681 |

OTHER PUBLICATIONS

U.S. Appl. No. 16/022,025, filed Jun. 28, 2018.

* cited by examiner

*Primary Examiner* — Kerri L McNally
(74) *Attorney, Agent, or Firm* — Leydig, Voit & Mayer, Ltd.

(57) ABSTRACT

A method for detecting allergic reaction and alerting a guardian device includes registering a wearable device to associate the wearable device with the guardian device. The wearable device then monitors vital signs to determine whether the vital signs are within an acceptable range. Based on the vital signs being outside the acceptable range, the wearable device sends an alert to the guardian device and determines whether a confirmation signal is received from the guardian device.

17 Claims, 7 Drawing Sheets

Heart Rate 702

Normal Heart Rate by Age (beats/minute)
Reference: PALS Guidelines, 2015

| Age | Awake Rate | Sleeping Rate |
|---|---|---|
| Neonate (<28 d) | 100-205 | 90-160 |
| Infant (1 mo-1 y) | 100-190 | 90-160 |
| Toddler (1-2 y) | 98-140 | 80-120 |
| Preschool (3-5 y) | 80-120 | 65-100 |
| School-age (6-11 y) | 75-118 | 58-90 |
| Adolescent (12-15 y) | 60-100 | 50-90 |

Respiratory Rate 704

Normal Respiratory Rate by Age (breaths/minute)
Reference: PALS Guidelines, 2015

| Age | Normal Respiratory Rate |
|---|---|
| Infants (<1 y) | 30-53 |
| Toddler (1-2 y) | 22-37 |
| Preschool (3-5 y) | 20-28 |
| School-age (6-11 y) | 18-25 |
| Adolescent (12-15 y) | 12-20 |

Blood Pressure 706

Normal Blood Pressure by Age (mm Hg)
Reference: PALS Guidelines, 2015

| Age | Systolic Pressure | Diastolic Pressure | Systolic Hypotension |
|---|---|---|---|
| Birth (12 h, <1000 g) | 39-59 | 16-36 | <40-50 |
| Birth (12 h, 3 kg) | 60-76 | 31-45 | <50 |
| Neonate (96 h) | 67-84 | 35-53 | <60 |
| Infant (1-12 mo) | 72-104 | 37-56 | <70 |
| Toddler (1-2 y) | 86-106 | 42-63 | <70 + (age in years x 2) |
| Preschooler (3-5 y) | 89-112 | 46-72 | <70 + (age in years x 2) |
| School-age (6-9 y) | 97-115 | 57-76 | <70 + (age in years x 2) |
| Preadolescent (10-11 y) | 102-120 | 61-80 | <90 |
| Adolescent (12-15 y) | 110-131 | 64-83 | <90 |

For diagnosis of hypertension refer to the NHBPEP Reference tables: http://www.nhlbi.nih.gov/health-pro/guidelines/current/hypertension-pediatric-jnc-4/blood-pressure-tables.

Temperature 708

Normal Temperature Range by Method
Reference: CPS Position Statement on Temperature Measurement in Pediatrics, 2015

| Method | Temperature (°C) |
|---|---|
| Rectal | 36.6-38 |
| Ear | 35.8-38 |
| Oral | 35.5-37.5 |
| Axillary | 36.5-37.5 |

Temperature ranges do not vary with age. Axillary, tympanic and temporal temps for screening (less accurate). Rectal and oral temps for definitive measurement (unless contraindication).

Oxygen Saturation 710

Normal pediatric pulse oximetry (SPO2) values have not yet been firmly established. SPO2 is lower in the immediate newborn period. Beyond this period, a SPO2 of <92% should be a cause of concern and may suggest a respiratory disease or cyanotic heart disease.

FIG. 7

DETECTING ALLERGIC REACTION AND ALERTING A GUARDIAN DEVICE

CROSS-REFERENCE TO RELATED APPLICATIONS

This application is a continuation of U.S. patent application Ser. No. 16/022,025, filed Jun. 28, 2018, which is incorporated by reference.

BACKGROUND

Several million American children suffer from moderate to severe allergic reactions due to food, insect stings, pollen or medications (especially antibiotics and radiocontrast agents used in imaging). Some of the allergic reactions in children or adults become fatal. Based on data from National Center for Health Statistics, there were about 2,500 fatal allergic reactions (anaphylaxis) from 2000 to 2010, and the number of fatal anaphylaxis keeps increasing every year. Oftentimes, children, who are prone to allergic reactions, are away from their parents or guardians, for example, the children may be at a playground, at their friends' homes, at a daycare, at a school, and so on. Under these circumstances, parents or guardians have no information on what is happening when their children undergo allergic reactions. Medication (such as epinephrine) must be dispensed to individuals within a few minutes from the onset of moderate to severe allergic reactions. Undetected severe allergic reactions may lead to loss of life.

SUMMARY

An embodiment of the disclosure provides a method, performed by a wearable device, for detecting allergic reaction and alerting a guardian device. The method comprises: (a) registering the wearable device to associate the wearable device with the guardian device; (b) monitoring vital signs to determine whether the vital signs are within an acceptable range; (c) based on the vital signs being outside the acceptable range, sending an alert to the guardian device; and (d) determining whether a confirmation signal is received from the guardian device.

An embodiment of the disclosure provides a computing device for monitoring allergic reaction. The computing device includes a processor to execute computer executable instructions stored on a non-transitory computer readable medium, so that when the instructions are executed, the computing device is configured to: (a) register a wearable device; (b) receive vital signs from the wearable device; (c) based on the vital signs being outside an acceptable range, display an alert from the wearable device; and (d) send a confirmation signal to the wearable device.

An embodiment of the disclosure provides a method for monitoring allergic reaction by a computing device. The method comprises: (a) registering a wearable device; (b) receiving vital signs from the wearable device; (c) based on the vital signs being outside an acceptable range, displaying an alert from the wearable device; and (d) sending a confirmation signal to the wearable device.

BRIEF DESCRIPTION OF THE DRAWINGS

FIG. 7 provides tables of normal vital sign ranges for different populations according to an embodiment of the disclosure.

DETAILED DESCRIPTION

Some fatal allergic reactions may be avoided, e.g., in the case of children, if detected proactively before the reactions become severe. Embodiments of the disclosure prevent fatalities due to allergic reactions by proactively monitoring vital signs, making intelligent inference from the vital sign readings, and alerting parents or guardians immediately. Embodiments of the disclosure provide an integrated system and apparatus for detecting onset of severe allergic reaction in children through a wearable device by combining changes to multiple vital signs, deriving inference, and alerting parents or guardians with details of the vital signs. The apparatus provides intelligent detection of allergic reaction by sensing and calculating deviation of vital signs from normal ranges using one or more sensors, for example, a pulse rate sensor, a respiratory rate sensor, an oxygenation level sensor, a body temperature sensor, and a skin conductance or a galvanic skin response sensor. The apparatus automates the alerting of parents or guardians by sending the alert to their mobile device. In some embodiments, the apparatus triggers an emergency response alert to have an emergency medical or ambulatory service dispatched to a child's location in the absence of any response from parents or guardians within a certain period after their mobile is device alerted. In some embodiments, the apparatus notifies parents or guardians when not in contact with the child or when unable to obtain vital signs of the child.

Figure 1:
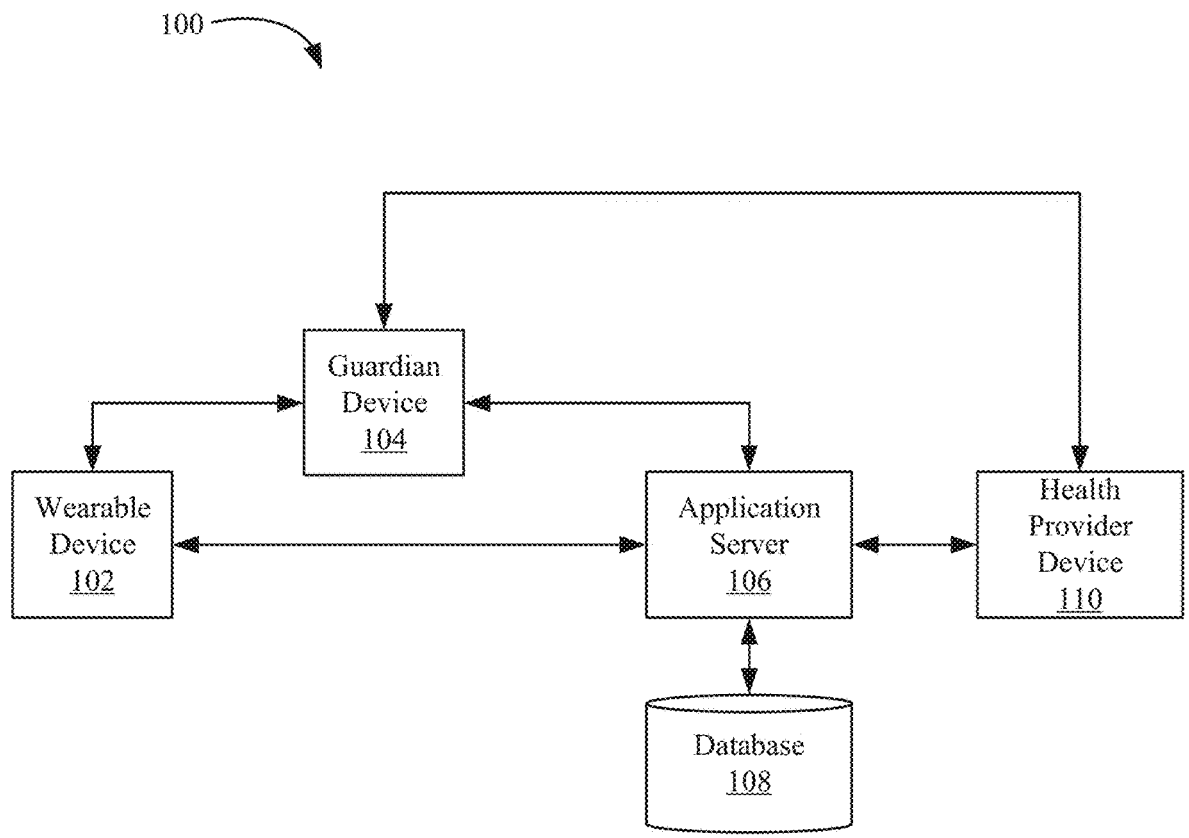
FIG. 1 illustrates a system for detecting allergic reaction according to an embodiment of the disclosure.

Embodiments of the disclosure are described in the context of a parent/guardian and child relationship, but it is understood that the embodiments may be used in any situation that has a guardian/caretaker and a dependent relationship. FIG. 1 illustrates a system 100 for detecting allergic reaction according to an embodiment of the disclosure. The system 100 may include a wearable device 102, a guardian device 104, an application server 106, one or more databases 108, and a health provider device 110. The wearable device 102 may be a wireless body area network (WBAN) including one or more sensor nodes, each configured to sense, sample, transform, process, and communicate physiological signals to the guardian device 104. A child wears the wearable device 102, and a parent or guardian operates the guardian device 104. The application server 106 supports a software application for the wearable device 102 installed on the guardian device 104. Database 108 stores additional configurations and data for the support of the software application. The health provider device 110 may include one or more devices for emergency services, hospitals, and so on. The guardian device 104 and health provider device 110 may include a smartphone, a tablet, a laptop, and so on.

The guardian device 104 runs a software application, e.g., a mobile application (a.k.a. App) which provides a user interface to the parent/guardian, and takes responsibility to transfer information about health status to the application server 106 at the backend through the Internet or mobile telephone networks, e.g., General Packet Radio Service (GPRS), 3G, when connected to the network. The application server 106 keeps record of registered users and provides current and historical information on vital signs and inferences captured by the wearable device 102 to various constituents—parents, guardians, first responders, physicians and hospitals depending on who has been authorized to view data. In addition to providing information on vital signs data, application server 106 stores information of registered users (parents/guardians) for the system, personal configuration information about the software application running on the guardian device 104 and general application specific information, such as application configuration, personalized settings, version executables and supplemental files, alerts and notifications.

Embodiments of the disclosure provide advantages to health care networks and sensor networks through network segmentation. By relying on the guardian device 104 and the application server 106 for data display, data processing, and long term data storage for trend analysis, the wearable device 102 can be manufactured to be a simpler device. By allowing the wearable device 102 to be a simpler device, wireless network protocols for data exchange between the guardian device 104 and wearable device 102 can be tailored based on amount of data to be transmitted and proximity of the guardian device 104 to the wearable device 102. In an example, if the wearable device 102 determines that the guardian device 104 is within range of a short distance wireless technology, the wearable device 102 opts to use the short distance wireless technology for data exchange. If the wearable device 102 determines that the guardian device 104 is not within range of the short distance wireless protocol, the wearable device 102 attempts connection with one or more longer distance technologies. By not focusing exclusively on one data exchange protocol, the wearable device 102 is able to mask data communication from wireless data sniffers parked on one data exchange protocol.

Figure 2:
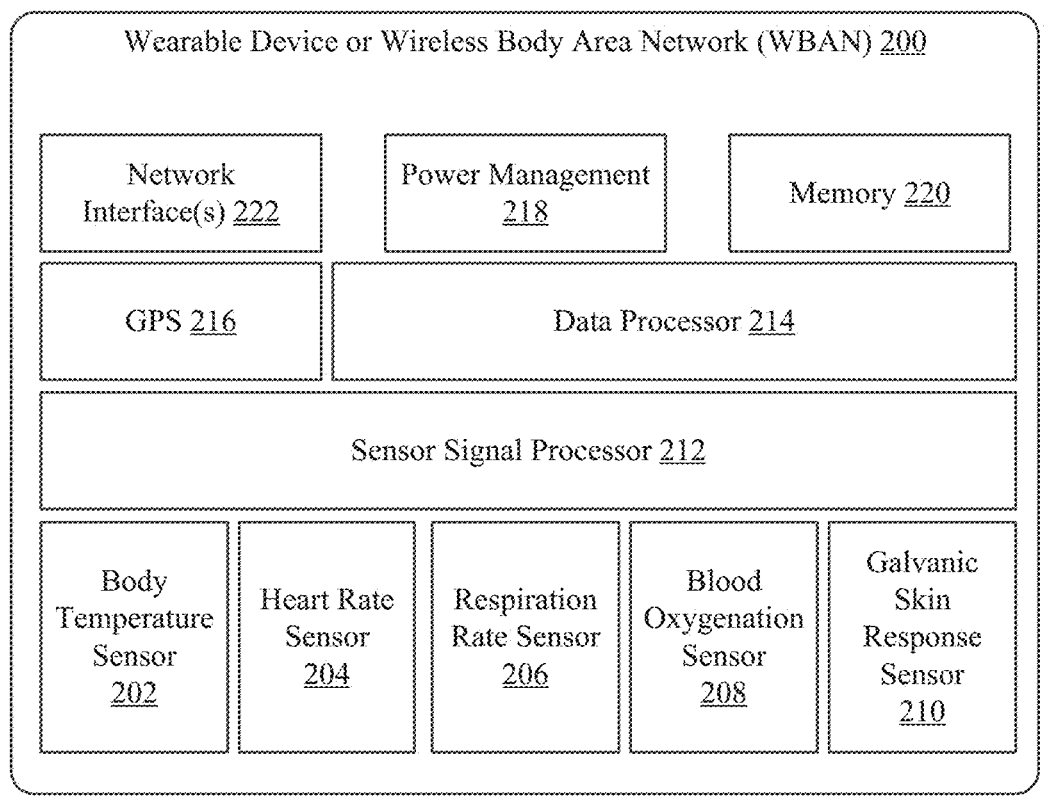
FIG. 2 illustrates a wearable device according to an embodiment of the disclosure.

FIG. 2 illustrates a wearable device 200 according to an embodiment of the disclosure. The wearable device 200 is an embodiment of wearable device 102. The wearable device 200 includes a number of intelligent nodes, each configured to sense, sample, transform and process, and communicate physiological signals (heart rate, blood pressure, body temperature, blood oxygen saturation level, respiration rate and galvanic skin conductance or response rate). The wearable device 200 may also include other components, depending on application for which it is being built for, and advanced algorithms for data extraction, processing, storage and decision making. The wearable device 200 includes one or more sensors, a sensor signal processor 212, a data processor 214, a global positioning system (GPS) receiver 216, a power management circuit 218, memory 220, and one or more network interfaces 222.

In an embodiment, the wearable device 200 includes one or more sensors. Example sensors provided in FIG. 2 include body temperature sensor 202 or thermometer, heart rate sensor 204, respiration rate sensor 206, blood oxygenation sensor 208, and galvanic skin response sensor 210. The blood oxygen sensor 208 may be a pulse oximeter sensor which may also measure hydration. The one or more sensors may further include optical and/or bio-impedance sensors. Bio-impedance sensors measure resistance of body tissue to tiny electric current circuit thus allowing the capture of a wide range of body signals. Optical sensors depend on change in volume of blood flowing through arteries, capillaries, or muscle tissues. In an embodiment, the one or more sensors of the wearable device 200 are integrated in one device worn, for example, on a child's wrist. The wearable device 200 may be a smart watch or an electronic device with a similar form factor. In another embodiment, the one or more sensors of the wearable device 200 are provided in a WBAN where each sensor is placed at a different location on the child's body. Each sensor when placed at a different location is termed a sensor node, and the sensor nodes each provide their respective physiological data to a head node.

The wearable device 200 includes a sensor signal processor 212. The sensor signal processor 212 is configured to collect, sample, and convert data from physical quantities to electrical signals through one or more analog-to-digital converters. The wearable device 200 further includes one or more network interfaces 222 which consist of network layer, media access control (MAC) layer, and wireless transceiver in the physical layer for communication among the one or more sensors and external devices, for example, a guardian device interfacing with the wearable device 200. The wearable device 200 further includes the power management circuit 218 configured to provide energy to the one or more sensors. The sensor signal processor 212, the data processor 214, network interfaces 222, power management circuit 218, and GPS 216 may be shared among the one or more sensors. The GPS receiver 216 establishes precise coordinates of a location of the wearable device 200. The GPS receiver 216 receives high-frequency, low-power radio signals from multiple satellites. The satellite signals are then translated into precise location coordinates based on a time it takes the signals to travel from the satellites to the wearable device 200.

The network interfaces 222 may support a low-complexity, low-cost, ultra-lower power, and highly-reliable wireless communication connectivity to upstream or downstream systems. Typical IEEE standards may be used including Bluetooth (IEEE 802.15.1) and Zigbee (IEEE 802.15.4) standards. Whereas IEEE 802.15.1 standard supports data-rates up to 250 Kbps, and covers a range of 1-10 m, IEEE 802.15.4 standard supports data-rates up to 2.1 Mbps, and covers a range of 1-100 m. In some embodiments, a child wearing the wearable device 200 may not be close to a smartphone or mobile device, as such, the network interfaces 222 supports transmitting emergency vital signs over wide area network (WAN) and cellular networks. Routine vital signs may be stored locally and transmitted to parents or guardians when the wearable device 200 is in the Wi-Fi zone. This minimizes the cost of communication over GPRS network. Therefore, the network interfaces 222 may use one or more communication protocols—IEEE 802.15.4, IEEE 802.11b and GPRS. IEEE 802.15.4 may be used for a personal area within close proximity, IEEE 802.11b used for a local area, and GPRS used for a wide area.

The data processor 214 fuses and filters data from the one or more sensors received from the sensor signal processor 212. The wearable device 200 may produce a large amount of physiological data, thus data fusion techniques combine data from the one or more sensors, filters noise, and makes inferences based on the combined data. During data fusion and filtering, the data processor 214 reduces redundancy in data collection which may result in reduced energy consumption of the wearable device 200.

The memory 220 may be a serial flash memory for buffering data and storing data on the wearable device 200 before transmitting to an external device. In some embodiments, the sensor signal processor 212, the memory 220, and the data processor 214 are provided on an ultra-low power microprocessor with built-in flash memory, random access memory (RAM), an analog-to-digital converter (ADC) for converting human physiological signals from analog to digital form for processing, and one or more analog channels that connect to the one or more sensors.

In an embodiment, the wearable device 200 includes an embedded operating system with minimal footprint, for example, TinyOS from University of Berkeley, Calif. The embedded OS is responsible for managing hardware components and communication within the wearable device 200. Additionally, the operating system fuses data and events from the one or more sensors, and controls power dissipation as power management may extend the life of a limited power source.

Figure 3:
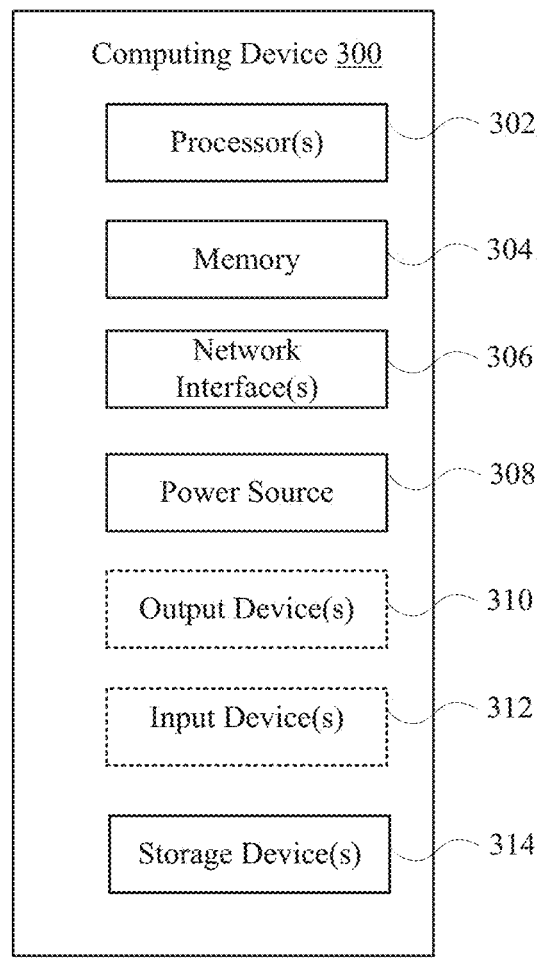
FIG. 3 illustrates components of a computing device according to some example embodiments.

FIG. 3 is a block diagram illustrating basic hardware components of a computing device 300 that may be used as the guardian device 104, application server 106, and the health provider device 110, according to some example embodiments. Computing device 300 may include one or more processors 302, memory 304, network interfaces 306, power source 308, output devices 310, input devices 312, and storage devices 314. Although not explicitly shown in FIG. 3, each component provided is interconnected physically, communicatively, and/or operatively for inter-component communications in order to realize functionality ascribed to the guardian device 104, application server 106, and the health provider device 110. To simplify the discussion, the singular form will be used for all components identified in FIG. 3, when appropriate, but the use of the singular does not limit the discussion to only one of each component. For example, multiple processors may implement functionality attributed to processor 302.

Processor 302 is configured to implement functions and/or process instructions for execution within the computing device 300. For example, processor 302 executes instructions stored in memory 304 or instructions stored on a storage device 314. In certain embodiments, instructions stored on storage device 314 are transferred to memory 304 for execution at processor 302. Memory 304, which may be a non-transient, computer-readable storage medium, is configured to store information within the device 300 during operation. In some embodiments, memory 304 includes a temporary memory that does not retain information stored when the device 300 is turned off. Examples of such temporary memory include volatile memories such as RAM, dynamic random access memories (DRAM), and static random access memories (SRAM). Memory 304 also maintains program instructions for execution by the processor 302 and serves as a conduit for other storage devices (internal or external) coupled to the computing device 300 to gain access to processor 302.

Storage device 314 includes one or more non-transient computer-readable storage media. Storage device 314 is provided to store larger amounts of information than memory 304, and in some instances, configured for long-term storage of information. In some embodiments, the storage device 314 includes non-volatile storage elements. Non-limiting examples of non-volatile storage elements include floppy discs, flash memories, magnetic hard discs, optical discs, solid state drives, or forms of electrically programmable memories (EPROM) or electrically erasable and programmable (EEPROM) memories.

Network interfaces 306 are used to communicate with external devices and/or servers. The computing device 300 may include multiple network interfaces 306 to facilitate communication via multiple types of networks. Network interfaces 306 may include network interface cards, such as Ethernet cards, optical transceivers, radio frequency transceivers, or any other type of device that can send and receive information. Non-limiting examples of network interfaces 306 include radios compatible with several Wi-Fi standards, 3G, 4G, Long-Term Evolution (LTE), Bluetooth®, etc.

Power source 308 provides power to the device 300. For example, the computing device 300 may be battery powered through rechargeable or non-rechargeable batteries utilizing nickel-cadmium or other suitable material. Power source 308 may include a regulator for regulating power from the power grid in the case of a device plugged into a wall outlet, and in some devices, power source 308 may utilize energy scavenging of ubiquitous radio frequency (RF) signals to provide power to the device 300.

The computing device 300 may also be equipped with one or more output devices 310. Output device 310 is configured to provide output to a user using tactile, audio, and/or video information. Examples of output device 310 may include a display (cathode ray tube (CRT) display, liquid crystal display (LCD) display, LCD/light emitting diode (LED) display, organic LED display, etc.), a sound card, a video graphics adapter card, speakers, magnetics, or any other type of device that may generate an output intelligible to a user of the computing device 300.

The computing device 300 may also be equipped with one or more input devices 312. Input devices 312 are configured to receive input from a user or the environment where the computing device 300 resides. In certain instances, input devices 312 include devices that provide interaction with the environment through tactile, audio, and/or video feedback. These may include a presence-sensitive screen or a touch-sensitive screen, a mouse, a keyboard, a video camera, microphone, a voice responsive system, or any other type of input device.

The hardware components described thus far for the device 300 are functionally and communicatively coupled to achieve certain behaviors. In some embodiments, these behaviors are controlled by software running on an operating system of the device 300.

Figure 4:
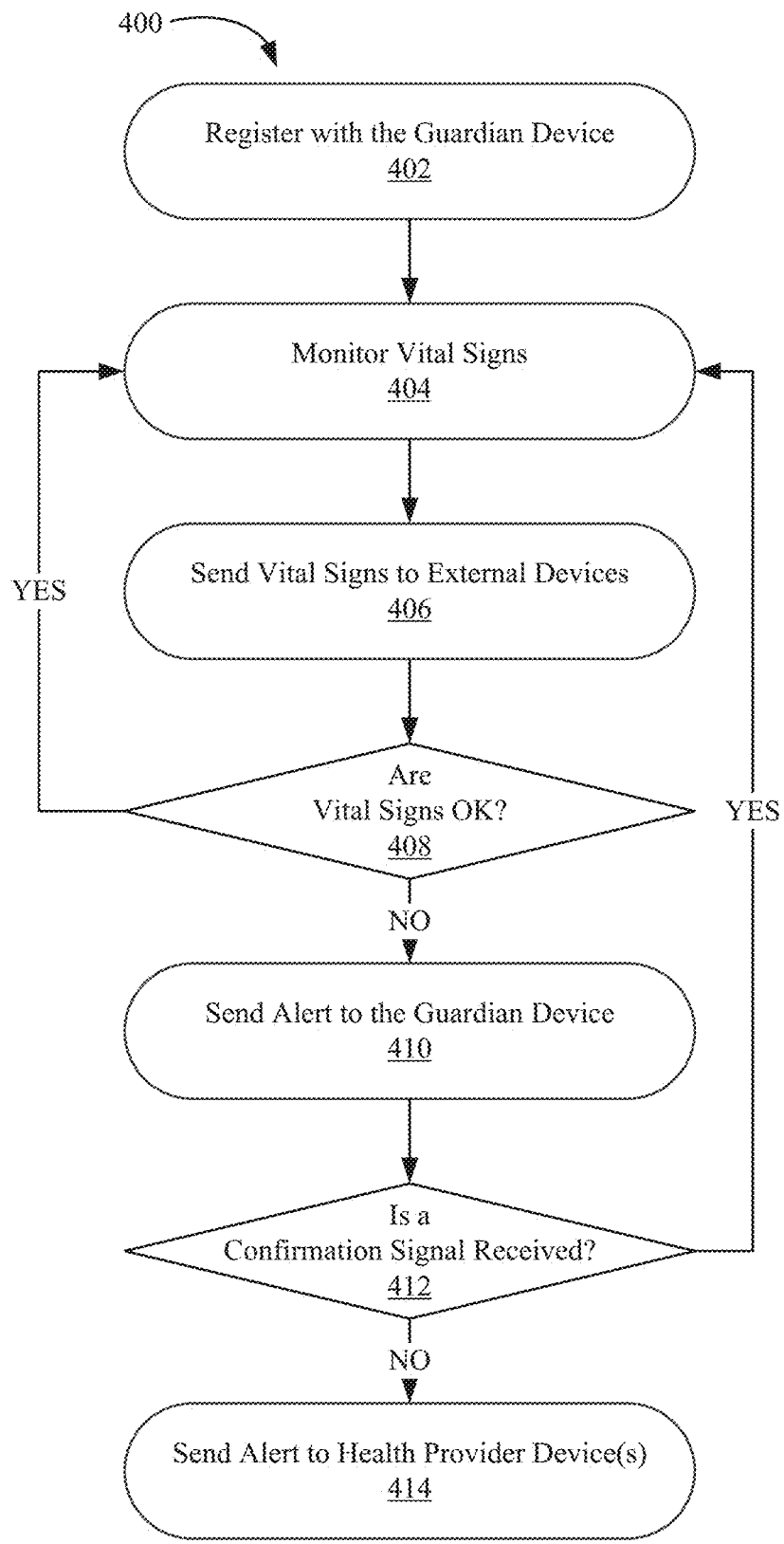
FIG. 4 is a flow diagram illustrating a process for detecting allergic reaction and alerting a guardian device according to an embodiment of the disclosure.

FIG. 4 is a flow diagram illustrating a process 400 for detecting allergic reaction and alerting a guardian device, according to an embodiment of the disclosure. At step 402, a wearable device, e.g., the wearable device 102 is registered with a guardian device, e.g., the guardian device 104. The registration at step 402 associates the wearable device 102 with the guardian device 104. The wearable device 102 is configured through a software application installed on the guardian device 104. In an embodiment, parameters configured on the software application include a serial number of the wearable device 102, a name and age of the child wearing the wearable device 102, an address associated with the wearable device 102, and telephone numbers. The parameters may further include a frequency of transmission of vital signs to the guardian device 104, e.g., vital signs may be set to be transmitted to the guardian device 104 every hour, or every 30 minutes, or every 5 minutes, or as the vital signs change significantly. The parameters configured on the software application may be stored on the application server 106. In an embodiment, the wearable device 102 retains in its memory two parameters: the serial number of the wearable device 102 and the age of the child.

In an embodiment, a button is activated on the wearable device 102 to perform a test of the association of the guardian device 104 with the wearable device 102. Once the button is activated, the wearable device 102 sends a test alert to the guardian device 104. Afterwards, the wearable device 102 receives a test response from the guardian device 102 indicating that the test of the association is completed. The test of association verifies that an alert can be properly communicated. Therefore, the test of association and reduces probability that an error will occur during an emergency.

In an example embodiment, at step 402, the application server 106 has pediatric vital signs reference data stored in database 108. Upon receiving the age of the child parameter from the software application running on the guardian device 104, the wearable device 102 requests an acceptable range for vital signs for children at that age. The wearable device 102 then receives one or more acceptable ranges for various vital signs for self-configuration. The acceptable ranges for vital signs for the child is stored on the flash memory of the wearable device 102. After storing the acceptable ranges, the wearable device 102 sends a handshake signal to the guardian device 104 with current vital signs readings of the child. The software application on the guardian device 104 and the wearable device 102 are thus synched up, and registration is complete. The wearable device 102 calibrates the acceptable range by taking a few sets of vital sign readings during different times on multiple days, storing the calibrated data in the flash memory. The calibrated range is sent to the application server 106 over cellular or Wi-Fi. The calibrated range acts as a threshold for calculating deviations or detecting onset of allergic reaction. Self-configuration to set the acceptable ranges allow the wearable device 102 to be tailored to a specific child, thus enhancing integrity of measurements obtained by the wearable device 102.

At step 404, the wearable device 102 monitors vital signs of the child to determine whether the vital signs are within the acceptable range. At step 406, the wearable device 102 sends the vital signs to external devices, e.g., the guardian device 104 or the application server 106. The wearable device 102 sends current vital signs of the child based on the frequency parameter set at step 402. The wearable device 102 may also include location coordinates (latitude and longitude) so that the guardian device 104 can display the vital signs information with color indicators and map the location coordinates to human-readable form (street address, city, and state). Color indicators showing vital signs in a green color when the vital signs are in an acceptable range and showing the vital signs in a red color when the vital signs are not in the acceptable range.

At step 408, the wearable device 102 determines whether the vital signs of the child are within the acceptable range. Based on the vital signs being within the acceptable range, the wearable device 102 continues monitoring the vital signs at step 404. Based on the vital signs being outside the acceptable range, the wearable device 102 sends an alert to the guardian device 104 at step 410.

At step 408, the wearable device 102 may determine different levels of severity and send appropriate alerts depending on the level of severity. For example, two levels of severity warrant an alert to be sent at step 410, the first level is an onset of low to moderate allergic reaction, and the second level is an onset of severe allergic reaction. When the wearable device 102 detects deviations of vital signs from an acceptable range, the wearable device 102 calculates standard deviation of body temperature, blood pressure, heart rate, respiratory rate and galvanic skin resistance or conductance. The wearable device 102 also checks the oxygen saturation level.

In the case of the onset of low to moderate allergic reaction, if body temperature, blood pressure, heart rate and respiratory rate are one standard deviation above the mean or acceptable range configured during calibration, and if blood oxygen saturation level drops to 80%, the wearable device 102 predicts that the child is undergoing low to moderate allergic reaction and sends an alert to the guardian device 104.

In the case of the onset of severe allergic reaction, if body temperature, blood pressure, heart rate and respiratory rate are two or more standard deviations above or below mean or acceptable range configured during calibration, and if the blood oxygen saturation level drops to 50-60% or below, the system predicts that the child is undergoing severe (anaphylactic) allergic reaction.

At step 410, alerting behavior may be different for the two levels of severity. For example, for the low to moderate allergic reaction, the guardian device 104 alerts the parent with intermittent beeps. Text displayed on the screen of the guardian device 104 may be colored in yellow. The alert may also include current vital signs of the child, location coordinates (latitude and longitude) and location coordinates mapped to human-readable form (street address, city and state). If there is no response or no confirmation signal received from the guardian device 104, the wearable device 102 will keep sending alerts after a waiting period, e.g., every 60 seconds, until the confirmation signal is received. The alert information (vital sign readings, location, response if received etc.) is recorded in the application server 106. For the severe allergic reaction, the guardian device 104 alerts the parent/guardian with blinking red-colored text in addition to sounding an alarm using a speaker of the guardian device 104. The alert may also include current vital signs of the child, location coordinates (latitude and longitude) and location coordinates mapped to human-readable form (street address, city and state). If there is no response or no confirmation signal received from the guardian device 104, the wearable device 102 continues to send alerts for a shortened waiting period, e.g., every 30 seconds, until the confirmation signal is received. The confirmation signal may be generated by clicking an "Alert Responded" message provided on the screen of the guardian device 104.

In some embodiments, in the severe allergic reaction case, when no confirmation signal is received in a predetermined amount of time, for example, 3 minutes, at step 412, an alert is sent to the health provider device 110.

In some embodiments, to minimize false allergic alerts, when the wearable device 102 does not detect any proper physiological signals from any of its sensors, the wearable device 102 provides a no connection alert to the guardian device 104. The no connection alert indicates to the parent/guardian that the wearable device 102 fails to measure vital signs. A no connection alert may be provided when the child is not wearing the wearable device 102 or when the child is improperly wearing the wearable device 102.

Figure 5:
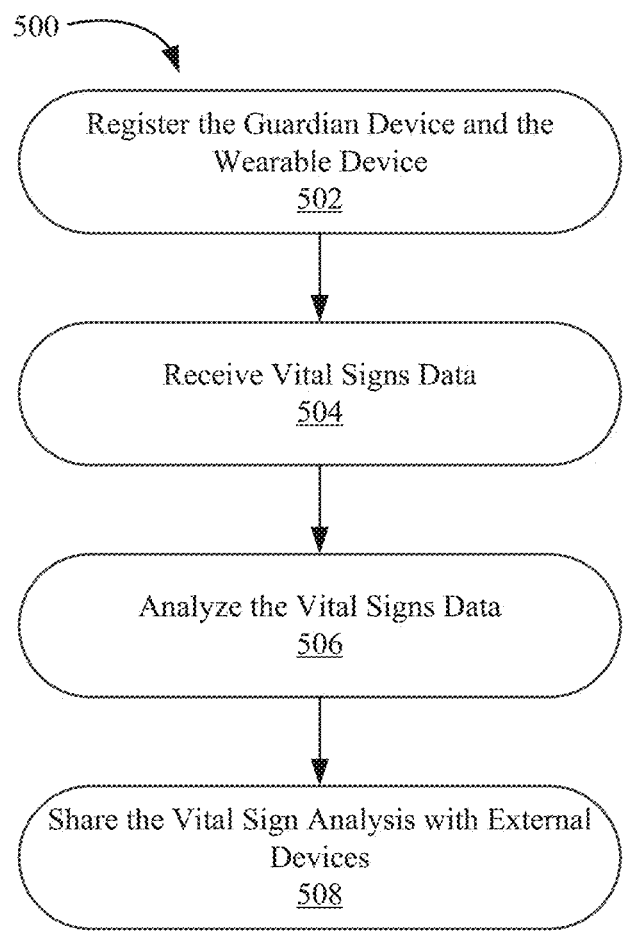
FIG. 5 is a flow diagram illustrating a process for providing allergic reaction data according to an embodiment of the disclosure.

FIG. 5 is a flow diagram illustrating a process 500, performed by the application server 106, for providing allergic reaction data, according to an embodiment of the disclosure. At step 502, the application server 106 receives configuration parameters registering the guardian device 104 with the wearable device 102. As previously discussed, these parameters may include a serial number of the wearable device 102, a name and age of the child wearing the wearable device 102, an address associated with the wearable device 102, and telephone numbers. The parameters may further include a frequency of transmission of vital signs and alerts to the guardian device 104, e.g., vital signs may be set to be transmitted to the guardian device 104 every hour, or every 30 minutes, or every 5 minutes, or as the vital signs change significantly. The parameters may further include software application settings and user preferences for the software application running on the guardian device 104. The parameters may further include healthcare providers or emergency services that a parent/guardian approves for sharing of vital signs data.

At step 504, the application server 106 receives vital signs data from the guardian device 104. In some embodiments, the application server 106 receives vital signs data from the wearable device 102. The vital signs data may include body temperature, blood pressure, heart rate, respiratory rate, and so on. The application server 106 may store the vital signs data in the database 108, and over time, accumulate historical values of the vital signs.

At step 506, the application server 106 performs analysis on the vital signs data obtained at step 504. The application server 106 may analyze combine current values of the vital signs with historical values of the vital signs to develop trend information. In some embodiments, since the application server 106 stores configuration data for multiple users and accumulates vital signs data for multiple wearable devices, the application server 106 can develop trend data based on one or more configuration parameters. For example, the application server 106 can develop vital signs trends or averages relating data accumulated from wearable devices associated with children of a specific age or a specific age range. For example, the application server 106 can develop vital signs trends for children in a specific household.

Historical data is accumulated for analyzing deviation of vital signs from a normal range. Frequency of deviation within a given time period (hours, days, weeks, months) can also be determined using time series analysis on the historical data.

At step 508, the application server 106 shares the vital sign analysis at step 506 with external devices, e.g., health provider device 110 or guardian device 104. In an embodiment, the application server 106 can accumulate historical data and send the historical data to the health provider device 110 so that a physician or any other healthcare provider can analyze deviation of vital signs. The deviation of the vital signs can be analyzed using time series analysis on the historical data. Time series graphs can depict data points indexed in time order. Thus, analyzing deviation and frequency will help healthcare providers in altering treatment options, including medication as well as informing parents or guardians about altering environment for their child.

Figure 6:
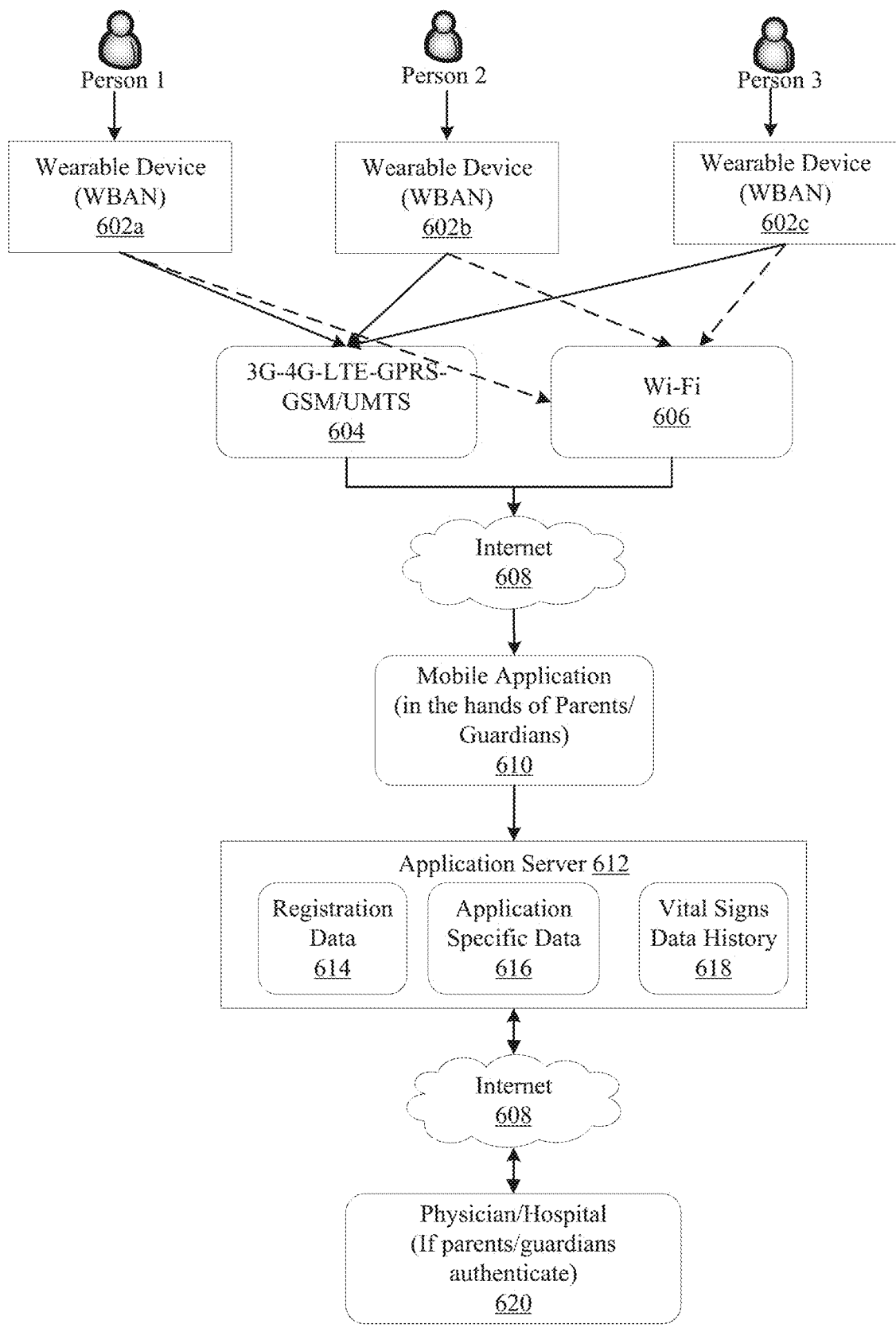
FIG. 6 illustrates a system for detecting allergic reaction according to an embodiment of the disclosure.

FIG. 6 illustrates a system for detecting allergic reaction according to an embodiment of the disclosure. FIG. 6 also depicts flow of information from a plurality of wearable devices (602a, 602b, and 602c) at the front-end of the user (persons 1-3 which are dependents) to the backend application server (application server 612). The wearable devices 602a, 602b, and 602c may be wearable device 200 as previously described. The wearable devices 602a, 602b, and 602c are shown to be compatible with a local network Wi-Fi 606 and a longer range network 604, e.g., 3G, 4G, LTE (Long Term Evolution), GPRS, GSM (Global System for Mobile Communication), or UMTS (Universal Mobile Telecommunications System).

Vitals data and/or alerts from the wearable devices 602a, 602b, and 602c are relayed through the internet 608 to a mobile application 610 running on a parent/guardian's device, e.g., the guardian device 104. The mobile application 610 communicates with the application server 612, e.g., the application server 106, on the backend. The application server 612 stores registration data 614, application specific data 616 (configuration and preferences for the parent/guardian), and vital signs data history 618. The application server 612 may provide trends, analysis, or vital signs data to a physician and/or hospital 620 through the internet 608.

A wearable device according to some embodiments of the disclosure can self-configure. Healthy or normal vital sign ranges vary depending on a child's age. A standard medical source, e.g., the tables provided in FIG. 7, provides normal range for vital signs for different age groups. In FIG. 7, table 702 provides example ranges for heart rate when a child is awake and when asleep and how these ranges differ for children of different age groups (neonate, infant, toddler, preschool, school-age, and adolescent). Table 704 provides an example range for respiratory rate and how this range differs for children of different age groups, e.g., infants, toddler, preschool, school-age, and adolescent. Table 706 provides example blood pressure ranges and how these ranges differ for children of different age groups and/or weight class. Table 708 provides example temperature ranges at different locations on a child. Table 710 provides a rule for determining a normal range for oxygen saturation in children that are not immediate newborns. Pediatric pulse oximetry (SPO2) values lower than 92% may suggest a problem for children that are not immediate newborns.

When a parent/guardian configures the mobile application, the mobile application will prompt the parent/guardian for age of the child who will wear the wearable device. During routine operational conditions, the mobile application will receive vital signs data from the wearable device multiple times through a few days. Using the received vital signs data, the mobile application along with the application server will learn a typical range for the particular child wearing the wearable device. The typical range for the particular child may be different from another child within his age range even though both children fall within the normal vital sign range prescribed in FIG. 7. The mobile application, in communication with the application server and the wearable device, thus sets up a baseline for vital signs (the typical range for the particular child) which will be used to calculate standard deviations of parameters.

In an embodiment, during onset of moderate allergic reaction, pertinent vital signs increase rapidly from the typical range for the particular child. For example, body temperature, pulse rate, blood pressure and respiratory rate increase rapidly which in turn causes emotional stress and the child starts to sweat. Sweat can be detected through galvanic skin response sensors measuring skin conductance. Additionally, blood oxygen saturation (SpO2) may start to decrease, as the child will have trouble breathing. The wearable device detects the rapid changes and also detects abnormal changes to vital signs beyond the child's acceptable range. Based on being beyond the acceptable range, the data processor of the wearable device combines and interprets the vital signs data, inferring that the child may be having a moderate to severe allergic reaction. In an embodiment, the following rule is used to determine the onset of moderate allergic reaction:

if [(StdDev (Body Temperature) >=1.0) AND (StdDev (Blood Pressure) >=1.0) AND (StdDev (Heart Rate) >=1.0) AND (StdDev (Respiratory Rate) >=1.0) AND (Blood Oxygen Saturation <0.8) AND (StdDev (Galvanic Skin Response) >=1.0)] then Onset of Moderate Allergic Reaction In an embodiment of the disclosure, during severe (anaphylactic) reaction, most vital signs fall rapidly from the typical or acceptable range. Oxygen Saturation (SpO2) also severely decreases during anaphylactic reaction to less than 30%. The wearable device detects the abnormal changes to the vital signs and the data processor of the wearable device combines and interprets the vital signs data, inferring that the child is experiencing severe allergic reaction. In an embodiment, the following rule is used to determine the onset of anaphylactic reaction:
if [(StdDev (Body Temperature) >=2.0) AND (StdDev (Blood Pressure) >=2.0) AND (StdDev (Heart Rate) >=2.0) AND (StdDev (Respiratory Rate) >=2.0) AND (Blood Oxygen Saturation <0.3) AND (StdDev (Galvanic Skin Response) >=2.0)] then Onset of Anaphylactic Reaction Due to some dependencies of vital signs collected, the example rules provided above for onset of moderate allergic reaction and anaphylactic reaction can be modified to trigger an alert when a specific vital sign is severely out of range. Thus, if one or more vital signs are out of range, then a general alert can be triggered even when either one of the rules is not met. This may be a safety feature for determining whether one or more of the sensors need to be calibrated or whether one or more of the sensors is failing. In the event of a confirmed failure, data from one or more sensors can be removed from the calculus when determining onset of moderate allergic reaction and anaphylactic reaction, and the example rules will ignore contribution or standard deviation of the failed sensors. Embodiments of the disclosure can adjust rules to account for specific sensor failures, thus making wearable devices on a network more resilient to failure.

Embodiments of the disclosure provide a wearable device that any child can wear on his/her wrist, similar to a fitness tracker or a smart watch, to detect onset of allergic reaction. Embodiments of the disclosure further provide a mobile application running on a parent/guardian's device that enables parents/guardians to visualize vital signs, e.g., pulse rate, respiratory rate, body temperature and oxygen level, transmitted by the wearable device and make calls to local emergency medical services or any of parents' friends or family to immediately attend to the child depending on the criticality of the vital signs. The mobile application is also used to configure the wearable device and, change system and user settings associated with the wearable device.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method, performed by a wearable device, for detecting abnormal vital signs and alerting a second device, the method comprising:
registering the wearable device to associate the wearable device with a second device;
detecting abnormal changes to at least one vital sign;
in response to detecting the abnormal changes to at least one vital sign, sending an alert to the second device;
determining whether a confirmation signal is received from the second device; and
resending the alert to the second device after a waiting period based on not receiving the confirmation signal, wherein the waiting period is longer when the abnormal changes to the at least one vital sign are moderate compared to when the abnormal changes to the at least one vital sign are severe.

2. The method according to claim 1, wherein the abnormal changes to at least one vital sign indicate an allergic reaction.

3. The method according to claim 1, wherein the second device is at least one of a guardian device and a health provider device.

4. The method according to claim 1, wherein registering the wearable device comprises:
associating one or more parameters with the wearable device, the parameters including a serial number of the wearable device, a name associated with the wearable device, an age associated with the wearable device, an address associated with the wearable device, telephone numbers, or a frequency of transmission of the vital signs.

5. The method according to claim 1, wherein registering the wearable device comprises:
receiving an age associated with the wearable device;
requesting an acceptable range for vital signs based on the age associated with the wearable device;
receiving the acceptable range for vital signs for self-configuration.

6. The method according to claim 1, further comprising:
sending vital signs data to the second device based on a frequency of transmission parameter, the vital signs data including current vital signs and location coordinates of the wearable device.

7. The method according to claim 1, wherein the vital signs are one or more measurements selected from the group consisting of: body temperature, blood pressure, heart rate, respiratory rate, and blood oxygen saturation level.

8. A wearable device for detecting allergic reaction and alerting a second device, the wearable device including a processor to execute computer executable instructions stored on a non-transitory computer readable medium, so that when the instructions are executed, the wearable device is configured to perform steps comprising:

registering the wearable device to associate the wearable device with a second device;

detecting abnormal changes to at least one vital sign;

in response to detecting the abnormal changes to at least one vital sign, sending an alert to the second device;

determining whether a confirmation signal is received from the second device; and resending the alert to the second device after a waiting period based on not receiving the confirmation signal, wherein the waiting period is longer when the abnormal changes to the at least one vital sign are moderate compared to when the abnormal changes to the at least one vital sign are severe.

9. The wearable device according to claim 8, wherein the abnormal changes to at least one vital sign indicate an allergic reaction.

10. The wearable device according to claim 8, wherein the second device is at least one of a guardian device and a health provider device.

11. The wearable device according to claim 8, wherein registering the wearable device comprises:

associating one or more parameters with the wearable device, the parameters including a serial number of the wearable device, a name associated with the wearable device, an age associated with the wearable device, an address associated with the wearable device, telephone numbers, or a frequency of transmission of the vital signs.

12. The wearable device according to claim 8, further configured to send the vital signs to the second device based on a frequency of transmission parameter, the vital signs including current vital sign measurements and location coordinates of the wearable device.

13. The wearable device according to claim 8, wherein the vital signs are one or more measurements selected from the group consisting of: body temperature, blood pressure, heart rate, respiratory rate, and blood oxygen saturation level.

14. The wearable device according to claim 8, further configured to:

send location coordinates from the wearable device, and map the location coordinates to human-readable form, the human-readable form including at least one of street address, city, and state information.

15. The wearable device according to claim 8, further configured to:

sound an alarm based on the vital signs being outside an acceptable range.

16. A non-transitory computer readable medium storing instructions, so that when the instructions are executed, a wearable device is configured to perform a method comprising:

registering the wearable device to associate the wearable device with a second device;

detecting abnormal changes to at least one vital sign;

in response to detecting the abnormal changes to at least one vital sign, sending an alert to the second device;

determining whether a confirmation signal is received from the second device; and resending the alert to the second device after a waiting period based on not receiving the confirmation signal, wherein the waiting period is longer when the abnormal changes to the at least one vital sign are moderate compared to when the abnormal changes to the at least one vital sign are severe.

17. The method according to claim 16, wherein registering the wearable device comprises:

associating one or more parameters with the wearable device, wherein the parameters include a serial number of the wearable device, a name associated with the wearable device, an age associated with the wearable device, an address associated with the wearable device, telephone numbers, or a frequency of transmission of the vital signs.

* * * * *